US008410326B2

(12) United States Patent
Dumesic et al.

(10) Patent No.: US 8,410,326 B2
(45) Date of Patent: Apr. 2, 2013

(54) INTEGRATED PROCESS AND APPARATUS TO PRODUCE HYDROCARBONS FROM AQUEOUS SOLUTIONS OF LACTONES, HYDROXY-CARBOXYLIC ACIDS, ALKENE-CARBOXYLIC ACIDS, AND/OR ALCOHOLS

(75) Inventors: James A. Dumesic, Verona, WI (US); David Martin Alonso, Madison, WI (US); Jesse Quentin Bond, Madison, WI (US); Dong Wang, Madison, WI (US); Ryan M. West, West Chester, OH (US)

(73) Assignee: Wisconsin Alumni Research Foundation, Madison, WI (US)

( * ) Notice: Subject to any disclaimer, the term of this patent is extended or adjusted under 35 U.S.C. 154(b) by 526 days.

(21) Appl. No.: 12/687,471

(22) Filed: Jan. 14, 2010

(65) Prior Publication Data
US 2011/0172476 A1    Jul. 14, 2011

(51) Int. Cl.
C07C 1/207 (2006.01)
C07C 1/213 (2006.01)
C07C 2/14 (2006.01)
(52) U.S. Cl. ......... 585/327; 585/324; 585/639; 585/520
(58) Field of Classification Search .................. 585/324, 585/327, 326, 639, 520
See application file for complete search history.

(56) References Cited

U.S. PATENT DOCUMENTS

| | | | |
|---|---|---|---|
| 3,131,234 A | | 4/1964 | Martin |
| 5,004,815 A | * | 4/1991 | Danheiser et al. ............ 549/328 |
| 5,883,266 A | | 3/1999 | Elliott et al. |
| 6,190,427 B1 | | 2/2001 | Ahmed |

FOREIGN PATENT DOCUMENTS

| | | |
|---|---|---|
| EP | 2055382 A1 | 5/2009 |
| WO | WO 2008/069987 A2 | 6/2008 |
| WO | WO 2009/079213 A2 | 6/2009 |
| WO | WO 2010/015733 A1 | 2/2010 |
| WO | WO 2010/151343 A1 | 12/2010 |

OTHER PUBLICATIONS

Gurbuz, E. I., et al., "Dual-bed catalyst system for C-C coupling of biomass-derived oxygenated hydrocarbons to fuel-grade compounds," *Green Chem.*, 2010, 12, 223-227.
Lange, J., et al., "Towards 'bio-based' Nylon: conversion of γ-valerolactone to methyl pentenoate under catalytic distillation conditions," *Chem. Commun.*, 2007, 3488-3490.
Noyce, D. S., et al., "The Stereochemistry of the Decarboxylation of β-Lactones to Form Olefins," *The Journal of Organic Chemistry*, vol. 31, No. 12, Dec. 1, 1966, pp. 4043-4047.

(Continued)

*Primary Examiner* — Thuan D Dang
(74) *Attorney, Agent, or Firm* — Joseph T. Leone, Esq.; Daniel A. Blasiole; DeWitt Ross & Stevens S.C.

(57) ABSTRACT

A process for producing hydrocarbons, especially $C_8$ or larger alkenes, from lactones, hydroxy-carboxylic acids, alkene-carboxylic acids, alcohols, or mixtures thereof, or an aqueous solution of lactones, hydroxy-carboxylic acids, alkene-carboxylic acids, alcohols, or mixtures thereof is described. The process includes reacting the starting materials with a first acid catalyst to yield a first product mixture. The first product mixture is then reacted with a second acid catalyst (which can be the same or different from the first acid catalyst) to yield a second product mixture comprising hydrocarbons, for example alkenes having a chain length of $C_{8+}$. The process is suitable for producing hydrocarbons that can be used in or as liquid transportation fuels.

23 Claims, 5 Drawing Sheets

OTHER PUBLICATIONS

West, R. M., et al., "Catalytic conversion of biomass-derived carbohydrates to fuels and chemicals by formation and upgrading of monofunctional hydrocarbon intermediates," Catalysis Today, vol. 147, No. 2, Sep. 30, 2009, pp. 115-125.

Serrano-Ruiz, Juan Carlos et al., "Catalytic upgrading of lactic acid to fuels and chemicals by dehydration/hydrogenation and C-C coupling reactions," Green Chemistry, 2009, pp. 1101-1104, vol. 11.

Benson, Tracy J., et al., "Heterogeneous Cracking of an Unsaturated Fatty Acid and Reaction Intermediates on H+ZSM-5 Catalyst," Clean, 2008, pp. 652-656, vol. 36(8).

Cejka, et al., Light naphtha conversion—isomerisation of $C_5$ and $C_6$ alkanes, Introduction to Zeolite Science and Practice, (Elsevier, $3^{rd}$ Revised Edition, 2007), pp. 895-899.

Centi et al., Catalysis for Renewables: From Feedstock to Energy Production (Wiley-VCH, Wienheim, 2007), pp. 137.

Coates et al., Discrete Metal-Based Catalysts for the Copolymerization of $CO_2$ and Epoxides: Discovery, Reactivity, Optimization, and Mechanism, Angew. Chem. Int. Ed, 43:6618-6639 (2004).

Cortright et al., Hydrogen from catalytic reforming of biomass-derived hydrocarbons in liquid water, Nature 418:964-967 (2002).

Darensbourg, D.J., Making Plastics from Carbon Dioxide: Salen Metal Complexes as Catalysts for the Production of Polycarbonates from Epoxides and $CO_2$, Chem. Rev. 107:2388-2410 (2007).

Fitzpatrick, S.W., Final Technical Report Commercialization of the Biofine Technology for Levulinic Acid Production from Paper Sludge, Tech. Report No. DOE/CE/41178 (BioMetics, Inc., 2002) http://www.osti.gov/bridge.

Haszeldine, R.S., Carbon Capture and Storage: How Green Can Black Be?. Science, 325:1647-1652 (2009).

Heeres et al., Combined dehydration/(transfer)-hydrogenation of C6-sugars (D-glucose and D-fructose) to γ-valerolactone using ruthenium catalyst, Green Chem. 11:1247-1255 (2009).

Horváth et al., γ-Valerolactone—a sustainable liquid for energy and carbon-based chemicals, Green Chem. 10:238-242 (2008).

Huber et al., Grassoline at the Pump, Sci. Am. 301:52 (Jul. 2009).

Huber et al., Synthesis of Transportation Fuels from Biomass: Chemistry, Catalysts, and Engineering, A. Chem. Rev. 106:4044-4098 (2006).

Huber, H.W., Breaking the Chemical and Engineering Barriers to Lignocellulosic Biofuels: Next Generation Hydrocarbon Biorefineries (U. Massachusetts Amherst, 2007). http://www.ecs.umass.edu/biofuels/Images/Roadmap2-08.pdf.

Koppatz. et al., $H_2$ rich product gas by steam gasification of biomass with in situ $CO_2$ absorption in a dual fluidized bed system of 8 MW fuel input, Fuel Processing Technology, 90:914-921.

Kunkes et al., Catalytic Conversion of Biomass to Monofunctional Hydrocarbons and Targeted Liquid-Fuel Classes, Science 322:417-421 (2008).

Lackner, K.S., A Guide to $CO_2$ Sequestration, Science 300 :1677-1678 (2003).

Mantilla et al., Oligomerization of isobutene on sulfated titania: Effect of reaction conditions on selectivity, Catal. Today 107-08, 707-712 (2005).

Manzer, L.E., Catalytic synthesis of α-methylene-γ-valerolactone: a biomass-derived acrylic monomer, Appl. Catal. A-General 272:249-256 (2004).

Matar et al., Chapter Nine: $C_4$ Olefins and Diolefins-Based Chemicals, Chemistry of Petrochemical Processes. (G.P. Company, Houston, ed. 2, 2000), pp. 248-250.

Mehdi et al., Integration of Homogeneous and Heterogeneous Catalytic Processes for a Multi-step Conversion of Biomass : From Sucrose to Levulinic Acid, γ-Valerolactone, 1,4-Pentanediol, 2-Methyl-tetrahrdrofuran, and Alkanes, Top. Catal. 48:49-54 (2008).

Quann et al., Chemistry of Olefin Oligomerization over ZSM-5 Catalyst, Ind. Eng. Chem. Res. 27:565-570 (1988).

Ragauskas et al., The Path Forward for Biofuels and Biomaterials, Science 311:484-489 (2006).

Sakurai et al., Synergism in Methanol syntehsis from carbon dioxide over gold catalysts supported on metal oxides, Catal. Today 29:361-365 (1996).

Simonetti et al., Coupling of glycerol processing with Fischer-Tropsch synthesis, Green Chem. 9:1073-1083 (2007).

Skupinska, J., Oligomerization of α-Olefins to Higher Oligomers, Chem. Rev 91:613-648 (1991).

Toyir et al., Catalytic performance for CO2 conversion to methanol of gallium-promoted copper-based catalysts: influence of metallic precursors. Appl. Catal. B-Environ. 34:255-266 (2001).

Wick et al., Pressure Measurement to evaluate ethanol or lactic acid production during glucose fermentation by yeast or heterofermentative bacteria in purer and mixed culture, Appl. Microbiol. Biotech. 56:687-692 (2001).

\* cited by examiner

INTEGRATED PROCESS AND APPARATUS TO PRODUCE HYDROCARBONS FROM AQUEOUS SOLUTIONS OF LACTONES, HYDROXY-CARBOXYLIC ACIDS, ALKENE-CARBOXYLIC ACIDS, AND/OR ALCOHOLS

FEDERAL FUNDING STATEMENT

This invention was made with government support under W911NF-09-2-0010 awarded by the ARMY/ARO. The government had certain rights in the invention.

FIELD OF THE INVENTION

Described is a process for converting lactones, hydroxy-carboxylic acids, alkene-carboxylic acids, alcohols, and mixtures thereof into hydrocarbons, as well as apparatus for carrying out the process.

BACKGROUND

Diminishing fossil fuel resources and increasing levels of $CO_2$ in the atmosphere require the development and implementation of strategies for the production of green, renewable transportation fuels (1-4). While first generation bio-fuels, such as corn ethanol and biodiesel, have the capacity to mitigate worldwide dependence on petroleum, new processes utilizing lignocellulosic biomass must be developed to produce sustainable bio-fuels at levels of worldwide demand (5). In this respect, GVL has been identified as a renewable platform molecule (6) with potential for impact as a feedstock in the production of both energy (6, 7) and chemicals (8). GVL is produced by hydrogenation of levulinic acid, the latter of which can be produced, potentially at low cost, from agricultural waste (3) using processes already established on a commercial scale (9). Recently, researchers have minimized the demand for an external source of hydrogen in this process by utilizing the formic acid formed in equi-molar amounts with levulinic acid from cellulose (7) and $C_6$ sugars (10). GVL retains 97% of the energy content of glucose and performs comparably to ethanol when used as a blending agent (10% v/v) in conventional gasoline (6). It has also been applied as a renewable co-solvent in splash blendable Diesel fuel (11). GVL suffers, however, from several limitations for widespread use in the transportation sector, such as high water solubility, blending limits for use in conventional combustion engines, and lower energy density compared to petroleum-derived fuels. These limitations can be at least partially alleviated by reducing GVL with an external source of hydrogen to produce methyltetrahydrofuran (MeTHF) (12), which can be blended up to 70% in gasoline.

SUMMARY

The limitations noted above with respect to using GVL (and other lactones) as a transportation fuel are completely eliminated by the present process, which converts lactones (such as GVL), as well as hydroxy-carboxylic acids, alkene-carboxylic acids, alcohols, or mixtures thereof, to liquid alkenes (or alkanes) with molecular weights targeted for direct use in or as gasoline, jet, and/or Diesel fuels.

Thus, a first version of the invention is directed to a process for producing hydrocarbons. The process comprises reacting lactones, hydroxy-carboxylic acids, alkene-carboxylic acids, alcohols, or mixtures thereof, or an aqueous solution comprising lactones, hydroxy-carboxylic acids, alkene-carboxylic acids, alcohols, or mixtures thereof with a first acid catalyst, at a first temperature, and a first pressure, to yield a first product mixture. The first product mixture is then reacted with a second acid catalyst, at a second temperature, and a second pressure, to yield a second product mixture comprising hydrocarbons. The second product mixture preferably comprises alkenes having a chain length of $C_8$ or greater. These alkenes can then be liquefied, and separated or partially purified from other compounds present in the second product mixture (most notably $CO_2$). These alkenes are suitable for use in or as transportation fuels.

It is preferred that after the first reaction (a ring-opening decarboxylation in the case of a lactone reactant, a decarboxylation in the case of a carboxylic acid reactant, or a dehydration in the case of an alcohol reactant) and before the second reaction (an oligomerization of alkenes present in the first reaction mixture) at least a fraction of any water present in the first product mixture is removed. It is generally preferred to remove as much water as possible or economically practical from the first product mixture before conducting the oligomerization reaction. The water separation step is optional if a water-tolerant catalyst is used in the second step, or if a neat reactant which does not yield water as a byproduct is used.

The first temperature and the second temperature, as well as the first pressure and the second pressure, may be the same or different. The first temperature preferably ranges from about 500 K to about 1000 K, more preferably from about 550 K to about 750 K, from more preferably still from about 600 K to about 700 K. The second temperature preferably ranges from about 300 K to about 800 K, more preferably from about 300 K to about 750 K, and more preferably still from about 350 K to about 600 K. The first pressure and the second pressure preferably range from atmospheric to about 100 bar, more preferably from about 15 bar to about 50 bar, and more preferably still from about 25 bar to about 45 bar Likewise, the first acid catalyst and the second acid catalyst may be the same or different. It is preferred that the first and second acid catalysts are solid acid catalysts.

The entire process is preferably conducted at a weight hourly space velocity of from about $0.05\,h^{-1}$ to about $5.0\,h^{-1}$.

The reactant can comprise any combination of lactones, hydroxy-carboxylic acids, alkene-carboxylic acids, alcohols, or mixtures thereof. There is no particularly preferred reactant, although lactones in general, and gamma-valerolactone in particular, yield product mixtures containing $C_{8+}$ alkenes, which are useful in formulating liquid transportation fuels.

Another version of the invention proceeds as described immediately above, but includes a final step of separating at least a fraction of any carbon dioxide present in the second product mixture. If the second reaction is conducted at elevated pressure, the $CO_2$ may be separated under pressure for subsequent use or sequestration.

It is preferred, although not required, that the process is conducted in an integrated reactor comprising a first reaction chamber in which step (a) is conducted, and a second reaction chamber, operationally connected to the first, in which step (b) is conducted. A phase separator may (optionally) be operationally disposed between the first reaction chamber and the second reaction chamber. The phase separator is configured to separate at least a fraction of any water present in the first product mixture before it is subjected to the second reaction.

Another version of the invention is directed to a process for producing alkenes having a chain length of $C_8$ or greater. Here, the process comprises reacting a reactant as described previously with a first acid catalyst, at a first temperature, and a first pressure, to yield a first product mixture; then separating from the first product mixture at least a fraction of any water present therein; and then reacting the first product mixture with a second acid catalyst, at a second temperature, and a second pressure, to yield a second product mixture comprising alkenes having a chain length of $C_8$ or greater. Here, the process is conducted in an integrated reactor comprising a first reaction chamber in which the first reaction is conducted; a phase separator in which the separation step is conducted (the phase separator being operationally connected to the first reaction chamber); and a second reaction chamber in which the second reaction is conducted (the second reaction chamber being operationally connected to the phase separator). The reaction conditions and catalysts are as described above.

Another version of the invention is directed to an apparatus for converting lactones, hydroxy-carboxylic acids, alkene-carboxylic acids, alcohols, or mixtures thereof, or an aqueous solution comprising lactones, hydroxy-carboxylic acids, alkene-carboxylic acids, alcohols, or mixtures thereof, to hydrocarbons. The apparatus comprises a first reaction chamber having an acid catalyst disposed therein, and configured to decarboxylate or dehydrate a reactant comprising lactones, hydroxy-carboxylic acids, alkene-carboxylic acids, alcohols, or mixtures thereof to yield a first product mixture comprising alkenes. This first reaction chamber is operationally connected to a phase separator configured to separate from the first product mixture at least a fraction of any water present therein. The phase separator is operationally connected to a second reaction chamber having an acid catalyst disposed therein, and configured to oligomerize alkenes in the first product mixture to yield a second product mixture comprising hydrocarbons having a chain length of $C_8$ or greater.

The apparatus may further comprise a second phase separator operationally connected to the second reaction chamber, wherein the second phase separator is configured to separate hydrocarbons present in the second product mixture from carbon dioxide present in the second product mixture.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices described herein can comprise, consist of, or consist essentially of the essential elements and limitations of the methods and devices described herein, as well as any additional or optional ingredients, components, or limitations described herein or otherwise useful in synthetic organic chemistry or chemical engineering.

DETAILED DESCRIPTION OF THE INVENTION

Abbreviations and Definitions

Figure 1:
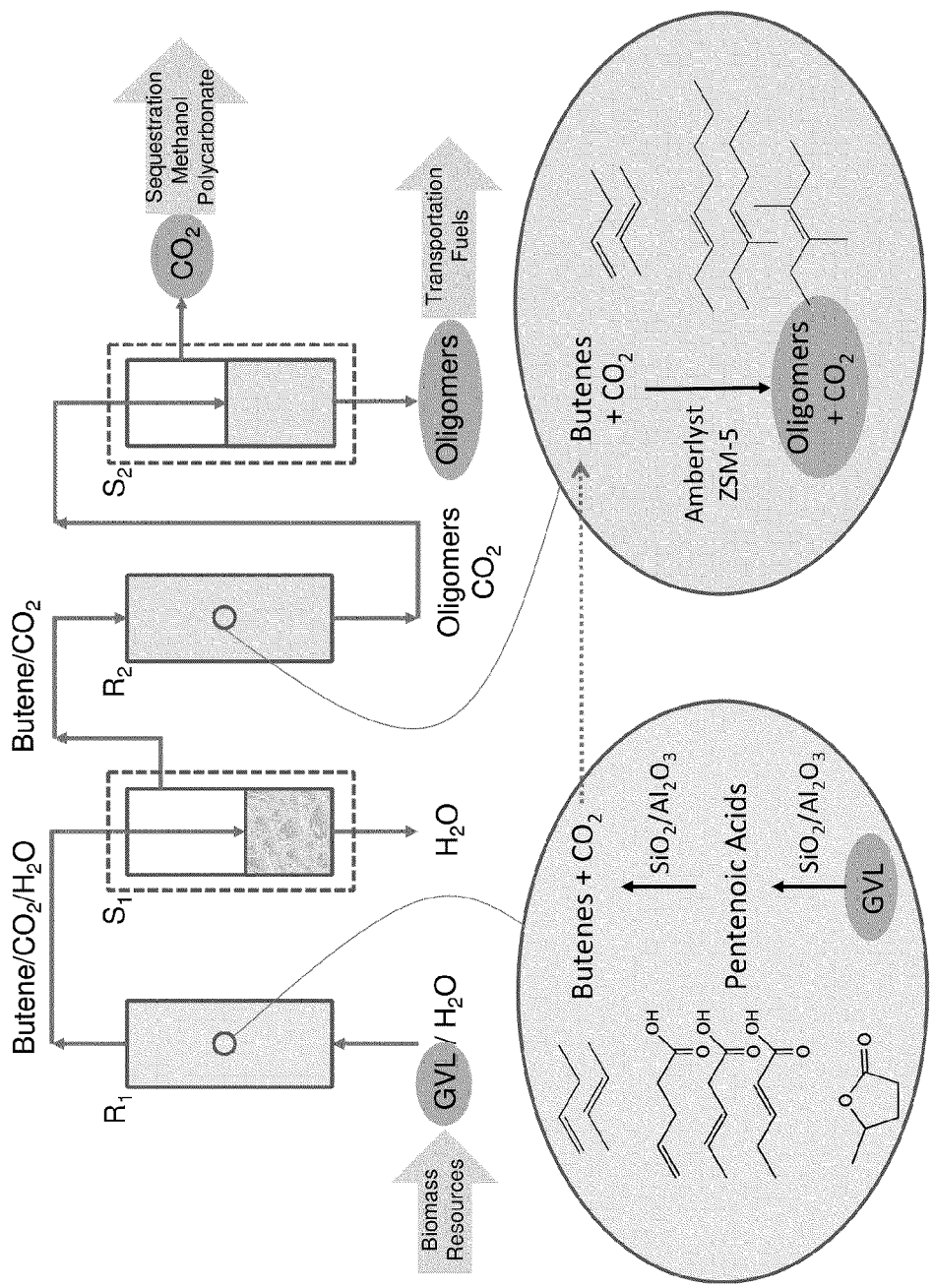
FIG. 1 is a schematic diagram illustrating reaction pathways for converting GVL to butenes and $CO_2$, and for converting GVL to a liquid stream of alkenes. The product alkenes may be used in or as transportation fuels.

The following abbreviations and definitions are used throughout the specification and claims. Terms not given a specific definition are to be accorded their accepted definition in the fields of chemistry and/or chemical engineering.

"Alcohol"=is any organic compound having two or more carbon atoms in which a hydroxyl functional group is bound to a carbon atom, preferably a $C_2$ to $C_{24}$-alcohol.

"Alkene-carboxylic acid"=any linear, branched, or cyclic alkenyl-containing carboxylic acid, preferably a $C_4$ to $C_{24}$-alkenyl-carboxylic acid, e.g., butenoic acid, pentenoic acid, 2-hexenoic acid, 3-hexenoic acid, etc. The definition includes carboxylic acids having more than one alkene moiety.

"Biomass"=any organic matter available on a renewable basis. As used herein, "biomass" explicitly includes (without limitation) forest and mill residues, agricultural crops and wastes, wood and wood wastes, grasses, non-crop plant matter, animal wastes, livestock operation residues, aquatic plants, trees and plants, and municipal and industrial wastes.

"Biomass-derived"=compounds or compositions fabricated or purified from biomass.

"FID"=flame ionization detector.
"GC"=gas chromatography.
"GVL"=gamma-valerolactone.
"ECL"=epsilon-caprolactone.
"Heteropolyacid"=a class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (−3) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure.

See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"HPLC"=high-pressure liquid chromatography.

"Hydrocarbons"=compounds comprised entirely of hydrogen and carbon atoms, including aliphatic (linear and branched) and cyclic alkanes, as well as aliphatic (linear and branched) and cyclic alkenes and alkynes having one or more unsaturations, including aromatic and non-aromatic compounds.

"Hydroxy-carboxylic acid"=any linear, branched, or cyclic hydroxy-containing carboxylic acid, preferably a $C_4$ to $C_{24}$-hydroxy-carboxylic acid, e.g., hydroxy-butanoic acids, citric acid, mandelic acid, and the like. The definition includes carboxylic acids having more than one hydroxy moiety.

Lactones: cyclic esters, including (without limitation), alpha-acetolactone, beta-propiolactone, gamma-butyrolactone, gamma-valerolactone, delta-valerolactone, epsilon-caprolactone, and the like.

"MS"=mass spectrometry.

"Operationally Connected" or "Operationally Disposed"=when referring to reactor components indicates that reactants, intermediate products, or final products can be moved from the upstream component to the downstream component (or vice-versa), but the two components need not be directly linked to one another. That is, there may be additional components disposed between reactor components that are "operationally connected."

"Solid Acid Catalyst"=Any solid acid catalyst, organic or inorganic, bearing Bronsted-Lowry and/or Lewis acid reaction sites. Exemplary solid acid catalysts acceptable for use herein include metal oxides and/or mixed metal oxides of the elements Li, Na, K, Mg. Ca, Zr, Ti, Mo, W, Fe, B, Al and Si; zeolites, metal or ammonium salts of mineral acids such as hydrochloric acid, sulfuric acid, nitric acid, phosphoric acid, or organic acids such as formic acid, acetic acid and sulfonic acids; cross-linked sulfonated polystyrene ion exchange resins such as "AMBERLYST"-brand resin (Rohm and Haas) and polyperfluorosulfonic acid resins such as "NAFION"-brand resin (E.I. du Pont de Nemours & Co., Wilmington, Del., USA), with or without silica nanocomposite; kieselguhr, alumina, titania or clays impregnated with a strong acid, such as acid clay, activated clay, bentonite, kaolin, talc, magnesium silicate, aluminum borate, and silicate; and sulfated zirconia, titania, and the like. Also included are metal-exchanged acid catalysts, such as Ni on silica/alumina, Cr on silica, etc.

"Space Velocity"=the mass/volume of reactant per unit of catalyst per unit of time.

"Support"=The catalysts described herein may be adhered to a support, such as silica, alumina, zirconia, titania, ceria, vanadia, carbon, heteropolyacids, silica-alumina, silica nitride, boron nitride, mixtures thereof, and the like. The foregoing list is illustrative, not exclusive. The active catalyst may be adhered to a nanoporous support, such as zeolites, nanoporous carbon, nanotubes, and fullerenes. The support itself may be surface-modified to modify surface moieties, especially surface hydrogen and hydroxyl moieties that may cause localized pH fluctuations. The support can be surface-modified by treating it with silanes, alkali compounds, alkali earth compounds, and the like. The surface chemistry of the support can also be modified by treatments that make it more acidic or basic, for example, by treating carbon supports with nitric acid or ammonia, respectively.

"TCD"=thermal conductivity detector.

"WHSV"=weight hourly space velocity=mass of reactant per mass of catalyst per h.

Overview:

Disclosed and claimed herein is a process and a corresponding apparatus to convert lactones, hydroxy-carboxylic acids, alkene-carboxylic acids, alcohols, or mixtures thereof, or an aqueous solution comprising lactones, hydroxy-carboxylic acids, alkene-carboxylic acids, alcohols, or mixtures thereof (which may be produced from biomass-derived carbohydrates) into liquid hydrocarbons in general, and alkenes in particular. Most notably, the process and apparatus, in its preferred version, are configured to convert the reactants to liquid hydrocarbons in the molecular weight range appropriate for transportation fuels, roughly about $C_8$ to $C_{24}$, and more preferably from about $C_8$ to about $C_{16}$, and most preferably any mixture of hydrocarbons comprising molecules having chain lengths of from about $C_8$ and longer (hereinafter referred to as ("$C_{8+}$ hydrocarbons"). The most preferred version of the process and concomitant apparatus uses an integrated catalytic system that does not require an external source of hydrogen. In short, the reactants, such as gamma-valerolactone (GVL), can be converted to a composition comprising $C_{8+}$ hydrocarbons (principally a mixture of $C_{8+}$ alkenes) without adding external hydrogen. The process comprises two steps. In the first step, the aqueous or neat feed is decarboxylated or dehydrated (in the case of an alcohol-containing feed). This can take place at ambient pressure or at elevated pressures, preferably greater than about 15 bar, preferably greater than about 25 bar, and more preferably still greater than about 35 bar (e.g., about 36 bar or more) and up to about 100 bar. The decarboxylation/dehydration step preferably takes place over a solid acid catalyst, such as a silica/alumina catalyst. When GVL is used as the feed, the first step yields a gas stream comprised of roughly equi-molar amounts of butene and carbon dioxide. This gas stream is then directly used in the second step of the process. In the second step, the gas stream from the first step is fed directly into a downstream oligomerization reactor containing an acid catalyst (e.g., HZSM-5, Amberlyst-70, etc.), which couples butene monomers in the first product mixture to form condensable hydrocarbons (principally alkenes) with molecular weights that can be targeted for gasoline, Diesel, and/or jet fuel formulations. The effluent gaseous stream of $CO_2$ at elevated pressure can be processed to mitigate greenhouse gas emissions from the process.

A specific benefit with respect to the present invention is that the combustion of biofuels is considered neutral with respect to emission of $CO_2$ into the atmosphere. This is because the $CO_2$ released during combustion of biofuels is balanced by $CO_2$ consumed as the carbon source to grow the biomass from which the fuel is derived (13). As shown in the stoichiometric relations below, the conversion of GVL to alkenes and $CO_2$ does not require an external source of hydrogen:

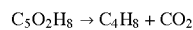
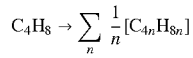

$$C_5O_2H_8 \rightarrow C_4H_8 + CO_2$$

$$C_4H_8 \rightarrow \sum_n \frac{1}{n}[C_{4n}H_{8n}]$$

(The hydrogenation of an alkene to an alkane requires one equivalent of $H_2$; however, the amount of $H_2$ required for the overall conversion of GVL to an alkane decreases as the molecular weight of the alkane increases.) While the combustion of biomass-derived alkenes is equivalent to the combustion of GVL in terms of energy, the combustion of alkenes made according to the present process leads to a net decrease in the level of $CO_2$ in the atmosphere by cycles of biomass growth and biofuel combustion, provided that the $CO_2$ formed during the conversion of GVL to alkenes could be utilized effectively. The same relationship can be used to describe the conversion of glucose to ethanol, as indicated in the stoichiometric relation below:

$$C_6O_6H_{12} \rightarrow 2C_2OH_6 + 2CO_2$$

However, an important difference between these two approaches for producing bio-fuels is that the production of $CO_2$ during the conversion of lactones, hydroxy-carboxylic acids, alkene-carboxylic acids, alcohols, or mixtures thereof as described herein is preferably performed at elevated pressure (e.g., preferably about 36 bar, as demonstrated in the Examples below). The $CO_2$ formed at such an elevated pressure is appropriate for sequestration (14, 15), conversion to methanol (16, 17) upon reaction with a renewable source of hydrogen (18, 19), or utilized for polycarbonate production via co-polymerization with epoxides (20, 21). In contrast, the production of $CO_2$ during fermentation of glucose to ethanol is carried out at atmospheric pressure in the presence of air (22). The resulting $CO_2$ is thus difficult to capture and compress for further use.

Preferred Process and Apparatus:

FIG. 1 is a schematic diagram showing one version of the integrated process and apparatus to convert an aqueous solution of GVL to liquid hydrocarbons with molecular weights appropriate for transportation fuels. As noted above, the process links the catalytic decarboxylation of GVL to butene and $CO_2$, to an oligomerization of the resulting butene, preferably at elevated pressures. Referring now to FIG. 1, the preferred apparatus uses a single catalytic system comprising two tubular flow reactors, $R_1$ and $R_2$ connected in series with an inter-reactor separator $S_1$. The first step comprises a ring-opening reaction of GVL to produce an isomeric mixture of unsaturated pentenoic acids. These then undergo decarboxylation to produce butene isomers and a stoichiometric quantity of $CO_2$ as shown in reference numeral 10 in FIG. 1. As demonstrated in the Examples presented herein, both the decarboxylation reaction and the oligomerization reaction can be carried out over a solid acid catalyst such as $SiO_2/Al_2O_3$, in the presence of water in a single, fixed bed reactor. The catalysts used in reactors $R_1$ and $R_2$ may be the same or different. Moreover, these reactions can be carried out at pressures ranging from ambient to 50 bar or more. After a separation step in which water is condensed to the liquid state in separator $S_1$, the butene/$CO_2$ gas stream is upgraded in a second reactor $R_2$ to a product comprising higher molecular weight alkenes through acid-catalyzed oligomerization (24, 25). This oligomerization process is favored at elevated pressures and can be tuned to yield alkenes with a targeted range of molecular weights and varied degrees of branching in the product stream (26, 27). In a second separation step, which takes place in separator $S_2$, the alkenes in the product gas stream are condensed to form a liquid product stream, while $CO_2$ remains as a high pressure gas. This approach does not require an external source of hydrogen, such as is necessary in the catalytic upgrading of bio-oils produced by pyrolysis of biomass (28).

Table 1, below, summarizes the effects of pressure, temperature, and feed composition for converting aqueous solutions of GVL to butene and $CO_2$ over a $SiO_2/Al_2O_3$ catalyst. For a given temperature (entries 1 to 3), the conversion of GVL is approximately constant at pressures ranging from 1 to 36 bar. The yield of butenes, however, decreases at higher pressures. Increased pressure has minimal effect on the ring-opening (conversion) of GVL. However, the rate of decarboxylation of the reactive intermediate, pentenoic acid (see FIG. 1, reference numeral 10), is hindered at elevated pressures. As system pressure increases, a loss of selectivity to butene was observed, along with a corresponding increase in selectivity to pentenoic acid. Thus, while not being limited to any underlying mechanism, it is proposed that GVL decarboxylation proceeds through acid-catalyzed protonation to cleave the cyclic ester linkage, followed by proton transfer leading to C—C bond scission and de-protonation to yield butene and an equivalent of $CO_2$ (see Schemes 1 and 2 in the Examples). The selectivity to butene can be improved by operating the reactor at higher temperatures, and good yields of butene (60%) were observed at 673 K and 36 bar (Table 1, entry 4). Higher temperatures tend to lead to coke formation, likely by polymerization of pentenoic acid, which causes catalyst deactivation with time on stream. Increasing the concentration of GVL in the feed has a positive effect on butene yield (Table 1, entries 5, 6), although coke formation eventually becomes a concern, leading to catalyst deactivation at GVL concentrations higher than about 80 wt % (see FIGS. 3 and 4 and the accompanying text in the Examples). Deactivation of $SiO_2/Al_2O_3$ is reversible, and catalytic activity can be restored by calcination at 723 K. Thus, the reactions can be run at temperatures above 673 K, although this is less preferred.

An appropriate (and preferred) compromise between obtaining a high rate of GVL conversion and maintaining stable catalyst operation is achieved using an aqueous feed solution containing about 60 wt % GVL at 648 K and at a pressure of about 36 bar (see Table 1, entry 5). Under these conditions, catalytic activity remains constant for over 100 h of time on stream (see FIG. 4 and the accompanying text in the Examples). Under these reaction conditions, the following yields were obtained: 85% conversion of the GVL feed to form butene and stoichiometric $CO_2$ (67% yield), pentenoic acid isomers (15% yield), small oxygenates such as butanol and propionaldehyde (2% yield), and aromatization/oligomerization products including octene and ethylbenzene (1% yield). The butene yield is limited by the unconverted pentenoic acid intermediate, and yields in excess of 90% are achieved using a 60 wt % feed at lower space velocities (Table 1, entry 7) with 100% of GVL conversion. Under these reaction conditions, pentenoic acid was not observed, and 93% yield to butene was achieved. The fraction of butene converted to $C_{8+}$ alkenes and aromatics increased and accounted for the remainder of products observed (7% yield). The percentage of butene present as 1-butene (33%) compared to cis/trans 2-butene (67%) was higher than thermodynamic equilibrium, suggesting that 1-butene is the primary product.

TABLE 1

GVL conversion and butene yield at different reaction conditions over a $SiO_2/Al_2O_3$ catalyst operating at a weight hourly space velocity (WHSV) equal to 0.9 h$^{-1}$

| Entry | T (K) | P (bar) | Feed GVL Concentration (wt %) | GVL conversion (%) | Butene Yield (%) |
|---|---|---|---|---|---|
| 1 | 648 | 1 | 30 | 97 | 75 |
| 2 | 648 | 18 | 30 | 94 | 65 |
| 3 | 648 | 36 | 30 | 70 | 35 |
| 4 | 673 | 36 | 30 | 95 | 60 |
| 5 | 648 | 36 | 60 | 85 | 67 |
| 6 | 648 | 36 | 80 | 99 | 96 |
| 7 | 648* | 36 | 60 | 99 | 93 |

*WHSV = 0.18 h$^{-1}$

The effluent from the GVL decarboxylation reactor ($R_1$ in FIG. 1) is a mixture of butene, $CO_2$, and water at elevated temperature and pressure. The mixture from $R_1$, comprising butene and $CO_2$, is then passed to the butene oligomerization reactor, $R_2$. (The $CO_2$ in the product mix from $R_1$ is not separated from the butene, but rather is passed, along with the butene, from $R_1$, through $S_1$, and into $R_2$. Water is not completely eliminated in $S_1$, so some water is also introduced into $R_2$ along with the $CO_2$ and butene.) In the preferred version of the process, $R_2$ is operated at a lower temperature than $R_1$ to favor alkene coupling and to minimize cracking reactions. This is preferred only, and not required. Although the oligomerization of alkenes is practiced widely in the petrochemical industry (24, 25, 29), no reports were found of processing butene/$CO_2$ mixtures in the presence of water at elevated pressures. Table 2 summarizes experimental results for butene oligomerization using HZSM-5 and Amberlyst-70 as catalysts. The conversion of butene over HZSM-5 reaches approximately 50% at ambient pressure and moderate temperature (Table 2, 523 K, entry 1). Higher conversions are achieved by increasing the reaction temperature to 573 K (Table 2, entry 2). However, a larger fraction of the products observed are low molecular weight alkenes, produced via cracking, and the selectivity for desired products ($C_{8+}$ alkenes for jet fuel applications) decreases from 80% to 55%. Increasing the pressure to 17 bar leads to an increase in the conversion of butene, accompanied by a decrease in selectivity for $C_{8+}$ alkenes (Table 2, entry 3). Higher selectivities (>88%) can be achieved at elevated pressure (17 bar) by decreasing the temperature to 498 K (Table 2, entry 4). A further decrease in temperature to 473 K leads to minimal improvement in selectivity but causes a decrease in butene conversion (Table 2, Entry 5). An increase in pressure to 36 bar at 498 K allows for high overall yields of $C_{8+}$ alkenes (77%) at high butene conversion (87%) (Table 2, entry 6).

Adding an equimolar co-feed of $CO_2$ to the butene oligomerization reactor leads to a decrease in butene conversion (Table 2, entry 7), while the selectivity to $C_{8+}$ alkenes remains unchanged. This decrease in butene conversion is likely caused by the corresponding decrease in butene partial pressure in the reactor, and the initial activity is restored upon removing $CO_2$ from the feed (Table 2, entry 8). It is possible to increase the conversion of butene to 90% in the presence of an equimolar amount of $CO_2$ without modifying the selectivity to $C_{8+}$ alkenes by decreasing the weight hourly space velocity (WHSV) to $0.09 \text{ h}^{-1}$ (Table 2, entry 9). Low levels of water in the feed decrease the conversion of butene from 90% to 82% (Table 2, entry 10). As the concentration of water in the oligomerization feed increases, inhibition becomes more pronounced, and only 47% of the butene is converted when equimolar quantities of butene, $CO_2$, and water are fed to the oligomerization reactor ($R_2$). When the water co-feed is stopped after 100 h time on stream, 96% of the initial activity is recovered, indicating reversible inhibition and long term stability. (See Examples.) In all experiments reported using HZSM-5 at 498 K, the selectivity to $C_{8+}$ alkenes is higher than 85%, indicating minimal extent of cracking.

It is possible to achieve complete butene conversion over Amberlyst-70 with high selectivity to $C_{8+}$ oligomers at elevated space velocities ($0.63 \text{ h}^{-1}$, Table 2, entry 14). The conversion of butene decreases upon introducing an equimolar cofeed of $CO_2$ (Table 2, entry 15), as found for HZSM-5. The inhibiting effect of water is minimal at low feed concentrations (Table 2, entry 16). As the fraction of water in the feed increases, inhibition becomes more pronounced and complete loss of activity is observed at high amounts of water (Table 2, entries 17, 18). When the co-feed of water is stopped

TABLE 2

1-Butene conversion, selectivity, and yield to liquid $C_8$-$C_{16}$ alkenes (hydrocarbons of appropriate molecular weight for direct use in liquid transportation fuels) and $C_{8+}$ alkenes (distribution includes all the above class in addition to all oligomers larger than $C_{16}$) over HZSM-5 and Amberlyst-70 catalysts.

| Entry | Catalyst | Feed Composition | T (K) | P (bar) | Butene Conversion (%) | Liquid selectivity ($C_8$-$C_{16}$)/$C_{8+}$ alkenes (%) | Liquid yield ($C_8$-$C_{16}$)/$C_{8+}$ alkenes (%) |
|---|---|---|---|---|---|---|---|
| 1* | HZSM-5 | Butene | 523 | 1 | 51 | 77/80 | 40/41 |
| 2* | HZSM-5 | Butene | 573 | 1 | 87 | 50/55 | 43/48 |
| 3* | HZSM-5 | Butene | 523 | 17 | 90 | 59/73 | 53/66 |
| 4* | HZSM-5 | Butene | 498 | 17 | 64 | 78/88 | 50/56 |
| 5* | HZSM-5 | Butene | 473 | 17 | 38 | 89/91 | 34/35 |
| 6* | HZSM-5 | Butene | 498 | 36 | 87 | 82/88 | 71/77 |
| 7* | HZSM-5 | Butene/$CO_2$ 50:50 | 498 | 36 | 64 | 77/85 | 49/54 |
| 8* | HZSM-5 | Butene | 498 | 36 | 90 | 80/89 | 72/80 |
| 9† | HZSM-5 | Butene/$CO_2$ 50:/50 | 498 | 17 | 90 | 65/88 | 58/79 |
| 10† | HZSM-5 | Butene/$CO_2$/$H_2O$ 47.5/47.5/5 | 498 | 17 | 82 | 72/89 | 59/73 |
| 11† | HZSM-5 | Butene/$CO_2$/$H_2O$ 45/45/10 | 498 | 17 | 72 | 72/86 | 52/62 |
| 12† | HZSM-5 | Butene/$CO_2$/$H_2O$ 33/33/33 | 498 | 17 | 47 | 79/89 | 37/42 |
| 13† | HZSM-5 | Butene/$CO_2$ 50:50 | 498 | 17 | 86 | 78/93 | 67/80 |
| 14‡ | Amberlyst 70 | Butene | 443 | 17 | 99 | 72/96 | 71/95 |
| 15‡ | Amberlyst 70 | Butene/$CO_2$ 50:50 | 443 | 17 | 93 | 69/95 | 64/88 |
| 16‡ | Amberlyst 70 | Butene/$CO_2$/$H_2O$ 47.5/47.5/5 | 443 | 17 | 90 | 74/95 | 66/86 |
| 17‡ | Amberlyst 70 | Butene/$CO_2$/$H_2O$ 45/45/10 | 443 | 17 | 50 | 85/92 | 43/46 |
| 18‡ | Amberlyst 70 | Butene/$CO_2$/$H_2O$ 33/33/33 | 443 | 17 | 0 | — | — |
| 19‡ | Amberlyst 70 | Butene/$CO_2$ 50:50 | 443 | 17 | 93 | 58/93 | 54/87 |

*WHSV = $0.11 \text{ h}^{-1}$.
†WHSV = $0.09 \text{ h}^{-1}$.
‡WHSV = $0.63 \text{ h}^{-1}$.

after 100 h time on stream, Amberlyst-70 regains 100% of its initial activity. (See Examples.)

Results from Tables 1 and 2 demonstrate that it is possible to couple GVL decarboxylation with butene oligomerization in a single system at elevated pressures, thereby reducing the overall capital expenditure that would be required to separate, purify and pressurize the butene obtained from GVL. This is a very distinct advantage of the present process. An additional advantage of the integrated system is that the vapor pressure of the $CO_2$ co-product formed by GVL decarboxylation is sufficiently high to achieve and sustain elevated system pressures appropriate for oligomerization. This increased pressure afforded by the $CO_2$ eliminates the need for external compression strategies in continuous operation. Because water has a strong negative effect on oligomerization, the reaction system depicted in FIG. 1 was designed to carry out the desired conversion of GVL to liquid alkenes by including a separation unit ($S_1$) between the GVL decarboxylation reactor ($R_1$) and the butene oligomerization reactor ($R_2$) to minimize the amount of water carried downstream. This preferred system allows for the delivery of a high pressure stream of gaseous butene from the first separator ($S_1$) to the inlet of the oligomerization reactor ($R_2$), while achieving removal of >98% of the water in the effluent from the decarboxylation reactor as a liquid. In the preferred configuration, the total pressure of the system is set at about 36 bar, a value that is appropriate for GVL conversion (see Table 1), as well as for butene oligomerization (see Table 2). The temperature of the inter-reactor separator $S_1$ is set at a value that is sufficiently low to liquefy most of the water for removal but sufficiently high to maintain butene in the gaseous state for transfer to the oligomerization reactor. The preferred temperature range for $S_1$ is thus roughly from about 373 to about 398 K. The products from the second reactor $R_2$ are collected in a second separator $S_2$, preferably operating at ambient temperature This yields a liquid effluent stream of $C_{8+}$ alkenes and unreacted butene, and a gaseous effluent stream of $CO_2$ with trace quantities of organic compounds.

Table 3 shows results for converting GVL and butene in the integrated catalytic system depicted in FIG. 1. (The product distributions for the liquid alkene effluent streams of these experiments are presented in Table 5 in the Examples.) The conversion of GVL and yield of butene in the first reactor $R_1$, as well as butene conversion and selectivity to liquid $C_{8+}$ alkenes in the second reactor $R_2$, are similar in the integrated system (Table 3, entry 1) to those values obtained for the isolated processes operating at similar conditions (see Tables 1 and 2), illustrating the reproducibility of the experiments. This experiment was carried out for 85 h (see FIG. 5 and the accompanying text in the Examples) while operating the inter-reactor separator $S_1$ at 373 K and a pressure of 36 bar, at which conditions no aqueous phase was observed in the effluent from the oligomerization reactor $R_2$, and the overall yield from GVL to $C_{8+}$ alkenes was 24%. This overall yield was limited by the decarboxylation of GVL and loss of butene in the first separation step.

TABLE 3

Performance of integrated catalytic system consisting of two flow reactors in series with an inter-reactor separator. Second reactor operated at 36 bar.

| | Reactor 1 (GVL to butene) | | | | Reactor 2 (Butene to alkenes) | | | | GVL to |
| --- | --- | --- | --- | --- | --- | --- | --- | --- | --- |
| Entry | T (K) | GVL conversion (%) | Butene yield (%) | Butene out of 1$^{st}$ separator (%) | Catalyst | T (K) | Butene conversion (%) | Liquid selectivity to ($C_8$-$C_{16}$)/$C_{8+}$ (%) | liquid ($C_8$-$C_{16}$)/$C_{8+}$ (%) |
| 1* | 648 | 63 | 37 | 75 | HZSM-5 (14 g) | 498 | 95 | 63/90 | 17/24 |
| 2† | 648 | 98 | 91 | 90 | HZSM-5 (14 g) | 498 | 44 | 76/86 | 28/31 |
| 3† | 648 | 99 | 92 | 88 | Amberlyst (3 g) | 443 | 92 | 74/94 | 50/62 |
| 4‡ | 648 | 99 | 90 | 89 | Amberlyst (4 g) | 443 | 94 | 64/93 | 48/66 |
| 5§ | 648 | 99 | 94 | 93 | Amberlyst (4 g) | 443 | 81 | 79/94 | 53/63 |
| 6∥ | 648 | 99 | 98 | 95 | Amberlyst (12 g) | 443 | 90 | 75/95 | 60/77 |

*Reactor 1: 2.7 g $SiO_2$—$Al_2O_3$. WHSV = 0.68 h$^{-1}$. First separator at 373 K.
†Reactor 1: 10 g $SiO_2$—$Al_2O_3$. WHSV = 0.18 h$^{-1}$. First separator at 383 K.
‡Reactor 1: 10 g $SiO_2$—$Al_2O_3$. WHSV = 0.18 h$^{-1}$. First separator at 388 K.
§Reactor 1: 10 g $SiO_2$—$Al_2O_3$. WHSV = 0.22 h$^{-1}$. First separator at 398 K.
∥Reactor 1: 8 g $SiO_2$—$Al_2O_3$. WHSV = 0.22 h$^{-1}$. First separator at 398 K.

To increase the total yield to liquid alkenes from GVL, experiments were carried out at lower space velocity of GVL (Table 2, entry 2) and higher separator temperature (383 K). At these conditions, GVL is almost quantitatively converted to butene with minimal formation of side products such as $C_{8+}$ alkenes and aromatics. Operating the separator at higher temperature increases the extent of both butene and water vaporization and subsequent delivery to the oligomerization reactor. The increased WHSV of butene in the second reactor, combined with the inhibiting effect of water, cause a decrease in butene oligomerization, although the total yield of $C_{8+}$ oligomers is improved to 31%.

Figure 2:
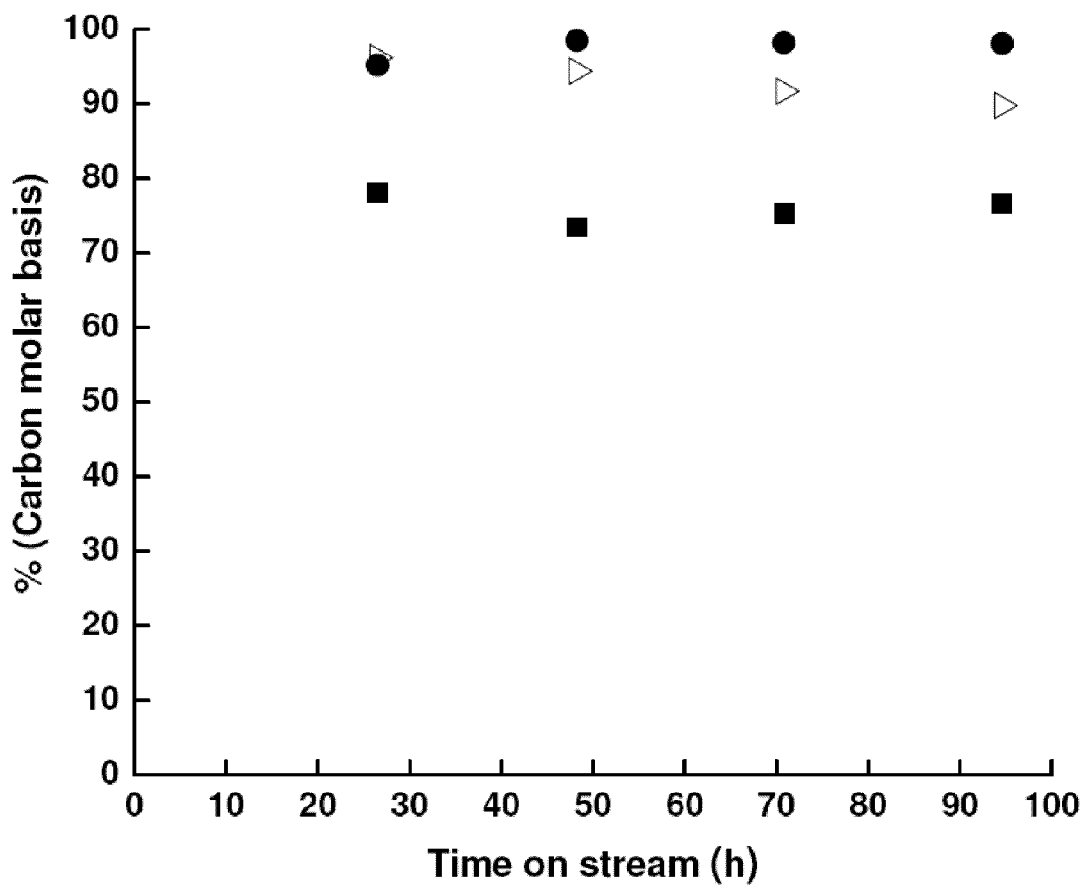
FIG. 2 is a graph depicting the yield of butene from GVL in reactor 1, butene conversion in reactor 2, and overall yield of liquid $C_{8+}$ alkenes from GVL in the integrated process described herein versus the time on stream. The first reactor operated at 36 bar (3.6 MPa), 648 K and 0.22 $h^{-1}$. The first separator operated at 36 bar (3.6 MPa) and 398 K. The second reactor operated at 36 bar (3.6 MPa), 443 K, and 12 g Amberlyst-70. The second separator operated at 36 bar (3.6 MPa), and 298 K. Butene yield (●), butene conversion (▷), yield to $C_{8+}$ alkenes (■).

Amberlyst-70 was identified to be a more active oligomerization catalyst than HZSM-5, and it can be used at lower temperatures to decrease the extent of cracking reactions and to improve the oligomerization selectivity to $C_{8+}$ alkenes (Table 2). Using Amberlyst-70 in the second reactor, the conversion of butene increases to 92%, with 94% selectivity to $C_{8+}$ alkenes. At these conditions the total yield of $C_{8+}$ alkenes from GVL increases to 62% (Table 3, entry 3). The total yield to $C_{8+}$ alkenes can be increased by decreasing the WHSV in the second reactor to increase the butene conversion (Table 3, entry 4). To maximize the amount of butene delivered to the second reactor the WHSV in the first reactor was increased from 0.18 to 0.22 h$^{-1}$, which decreases decarboxylation by-products, such as higher alkenes and aromatics, and increases the butene yield to 94%. Additionally, by operating the initial separator at 398 K, 94% of the butene formed is delivered to the oligomerization reactor (Table 3, entry 5). The higher separator temperature increases the amount of water in the second reactor, which inhibits butene oligomerization (81% conversion) and results in an overall yield of $C_{8+}$ alkenes equal to 63%. A final yield over 75% can be achieved by increasing the amount of catalyst in the second reactor to compensate for water inhibition and reducing the amount of catalyst in the first reactor to maintain the same WHSV (Table 3, entry 6). Under these conditions, the integrated catalytic system depicted in FIG. 1 operates for more than 90 h of time on stream (see FIG. 2) with high conversions of GVL and butene in the first ($R_1$) and second ($R_2$) reactors, respectively, and with a high overall yield to $C_{8+}$ alkenes (>75%). Increasing the amount of catalyst in the oligomerization reactor modifies the selectivity, decreasing the $C_8$-$C_{16}$ fraction and increasing the percentage of larger alkenes (see Table 5 and the accompanying text in the Examples).

The integrated reactor shown in FIG. 1 (which is the preferred version of the reactor) comprises two reactors ($R_1$ and $R_2$) which are preferably flow reactors, two phase separators ($S_1$ and $S_2$), and a simple pumping system (not shown) for delivering a reactant solution comprising an aqueous solution of GVL to the $R_1$ reactor. Suitable conduit, as shown in FIG. 1, connects $R_1$ to $S_1$ to $R_2$ to $S_2$. This arrangement of elements minimizes secondary processing steps and required equipment (e.g., purification of feeds, compression of gases, and pumping of gases). Additionally, the process and apparatus does not require the use of precious metal catalysts, further decreasing capital costs. The catalytic system described herein provides an efficient and inexpensive processing strategy for GVL. The cost of producing either butene or jet fuel using the process described herein would be dictated in major part by the market cost of GVL, rather than capital costs for the equipment and catalysts required to accomplish the conversions.

EXAMPLES

The following Examples are included solely to provide a more complete description of the processes disclosed and claimed herein. The Examples do not limit the scope of the claims in any fashion.

Catalyst Preparation:

Amorphous $SiO_2/Al_2O_3$ ("SIAL 3113"-brand) used in the ring opening/decarboxylation of GVL was obtained from Grace-Davison/Davicat (Columbia, Md., USA, a wholly-owned subsidiary of WR Grace & Co.). Prior to reaction kinetics studies, the $SiO_2/Al_2O_3$ catalyst was dried in situ under flowing air at 623 K. HZSM-5 zeolite (Si:Al=14) used in the oligomerization of butene was obtained from Engelhard/BASF AG (Ludwigshafen, Germany) and conditioned via thermal calcination at 773 K under flowing air prior the catalytic experiments. "AMBERLYST-70"-brand polymer catalyst used in the oligomerization of butene was obtained from Rohm and Haas (Philadelphia, Pa., USA, a wholly-owned subsidiary of Dow Chemical Company). Prior to reaction, it was rinsed with de-ionized water until the effluent showed no signs of residual acidity and dried overnight at 393 K.

Decarboxylation Studies:

The ring opening/decarboxylation of GVL was carried out in an up-flow fixed-bed reactor. The catalyst was loaded into a ¼" (64 mm) tubular stainless steel reactor. When necessary the catalyst was mixed with crushed granules of fused silica to fill the reactor volume. The catalyst bed was held in place by two plugs of quartz wool, and the reactor was mounted inside an aluminum block placed within a well-insulated furnace (Applied Test Systems, Inc., Butler, Pa., USA). Reactor pressure was controlled with a back pressure regulator (GO Regulator Inc., model BP-60, Spartanburg, S.C., USA). Reaction temperature was monitored at the reactor wall by a Type K thermocouple (Omega Engineering, Inc., Stamford, Conn., USA) mounted within the aluminum block and controlled by a Series 16 temperature controller (Love Controls, Michigan City, Ind., USA a division of Dwyer Instruments, Inc.). Prior to introducing the feed, the desired reaction temperature and pressure were achieved under flowing inert gas (He). Gas flow to the reactor was controlled using Brooks Mass Flow Controllers (Brooks Instrument, Hattfield, Pa., USA, Model 5850S). Upon reaching the desired reaction conditions, an aqueous solution of GVL (30-80 wt %) was prepared and fed to the packed tubular reactor using an HPLC pump (Lab Alliance, State College, Pa., USA, Series I). For experiments requiring a pure feed, GVL was used as received from the supplier (Sigma-Aldrich, St. Louis, Mo., USA). Liquid effluent was collected for quantitative analysis in a separator (Jerguson Gage and Valve, Strongsville, Ohio, USA) at ambient temperature and analyzed by GC (GC-2010 with FID detector, Shimadzu Scientific Instruments, Kyoto, Japan, and Columbia, Md., USA). Unknown product peaks were identified using GC-MS (Shimadzu GCMS-QP2010S). CO and $CO_2$ in the gas effluent were quantified using a Shimadzu GC-8A equipped with a TCD detector. Gas-phase alkenes and alkanes were quantified using a Varian "Star 3400 CX"-brand GC (Varian, Inc., Palo Alto, Calif., USA) equipped with an FID detector. Selectivities and yields were calculated on a molar carbon basis. Total carbon balances for the production of butene from GVL typically closed to within 10%.

To probe the mechanism of decarboxylation over $SiO_2/Al_2O_3$, additional studies were carried out using the above protocol with several relevant feeds such as pentanoic acid, 2-, 3-, 4-pentenoic acids, and gamma-valerolactone (GVL) and delta-valerolactone (DVL). The $SiO_2/Al_2O_3$ catalyst was calcined under flowing air at 723 K prior to introducing a new feed. Water soluble lactones were introduced in aqueous solution (20 wt %) using an HPLC pump (Lab Alliance Series I), and sparingly soluble organic acids were introduced using a syringe pump (Harvard Apparatus) along with a co-feed of de-ionized water introduced via a HPLC pump to yield a feed of 20 wt % organic compound. Analytical methods were identical to those listed above and carbon balances closed to within 10%.

Butene Oligomerization:

The oligomerization of butene was carried out in a down-flow fixed-bed reactor. The catalyst was loaded into a ½" (12.7 mm) tubular stainless steel reactor. The catalyst bed was held in place by two plugs of quartz wool, and the reactor was mounted inside an aluminum block placed within a well-insulated furnace (Applied Test Systems). Reactor pressure was controlled with a back pressure regulator (GO BP-60). Reaction temperature was monitored at the reactor wall by a Type K thermocouple (Omega) mounted within the aluminum block and controlled by a Series 16 temperature controller (Love Controls). Prior to introducing the feed, the desired reaction temperature and pressure were achieved under flowing inert gas (He). Gas flow to the reactor was controlled using Brooks Mass Flow Controllers (Model 5850S). 1-Butene (CP grade, Airgas, West Chicago, Ill., USA) was fed to the packed tubular reactor as gas, using a Brooks Mass Flow Controller (Model 5850S), or as liquid using a high pressure syringe pump (model 290D, Teldyne-Isco, Lincoln, Neb., USA) depending on experimental conditions. To simulate the gas effluent from the GVL decarboxylation reaction, $CO_2$ (Praxair, Danbury, Conn., USA) was introduced to the oligomerization reactor using a needle valve to control the flow. To simulate carryover of water vapor into the oligomerization reactor, deionized water was introduced as a co-feed using a high-pressure syringe pump (Harvard Apparatus, Holliston, Mass., USA). The liquid effluent was collected for quantitative analysis in a separator (Jerguson Gage and Valve) at ambient temperature and analyzed by GC (Shimadzu GC-2010 with FID detector). Unknown product peaks were identified using GC-MS (Shimadzu GCMS-QP2010S). Gas-phase products were analyzed for alkanes and alkenes as well as $CO_2$ using an in-line pair of gas chromatographs (Shimadzu GC-2010 equipped with an FID detector and Shimadzu GC-8A equipped with a TCD detector). Selectivities and yields were calculated on a molar carbon basis. Total carbon balances for the production of butene from GVL typically closed to within 10%.

Process Integration:

One version of the preferred integrated catalytic system for converting GVL to olefins at elevated pressures comprises two flow reactors in series with an inter-reactor separator to remove liquid water. An aqueous solution of GVL was fed to the first reactor, and the effluent from the first reactor was directed to a high-pressure vapor-liquid separator wherein liquid water, unreacted GVL and other by-products such as pentenoic acid were separated from vapor-phase products (butene, carbon dioxide). The separator and all of the tubing from the separator to the second reactor were heated to provide a dry, high-pressure feed of butene to the oligomerization reactor. Temperature measurements were made using a Type K thermocouple with temperature control provided by a Series 16 controller (Love Controls). The high-pressure gas stream from the first separator was fed to the second reactor, and the effluent of this second reactor was collected in a vapor-liquid separator (Jerguson Gage and Valve) at ambient temperature. Total system pressure was controlled using a back pressure regulator (GO, model BP-60) at the outlet of the second separator. Gas-phase products were delivered to a pair of in-line gas chromatographs (Shimadzu GC-2010 and Shimadzu GC-8A) for analysis of alkanes, alkenes, and $CO_2$ content. See FIG. 1 (discussed earlier) for the basic set-up.

The liquid phase effluents from both separators were collected in sealed containers (such that mass loss via vaporization and out-gassing of the hot liquid stream could be quantified). Some of the $CO_2$ and butene produced in the first reactor remains as soluble gas in the water collected in the first separator due the high pressure of the system. In the second separator, some of the unconverted butene remains condensed at high pressure, but vaporizes when the system is opened to atmospheric pressure for sampling. Vapor-phase products were analyzed by a pair of gas chromatographs (a Varian Star 3400 CX equipped with an FID detector and a Shimadzu GC-8A equipped with a TCD detector) to quantify alkanes, alkenes, and $CO_2$ out-gassed in sampling the liquid phases. The remaining liquid composition was quantified using a Shimadzu GC-2010 with an FID detector. Product identification was carried out using a Shimadzu GC-MS (Shimadzu GCMS-QP2010S). Carbon balances over the entire system closed to within 10%.

Figure 3:
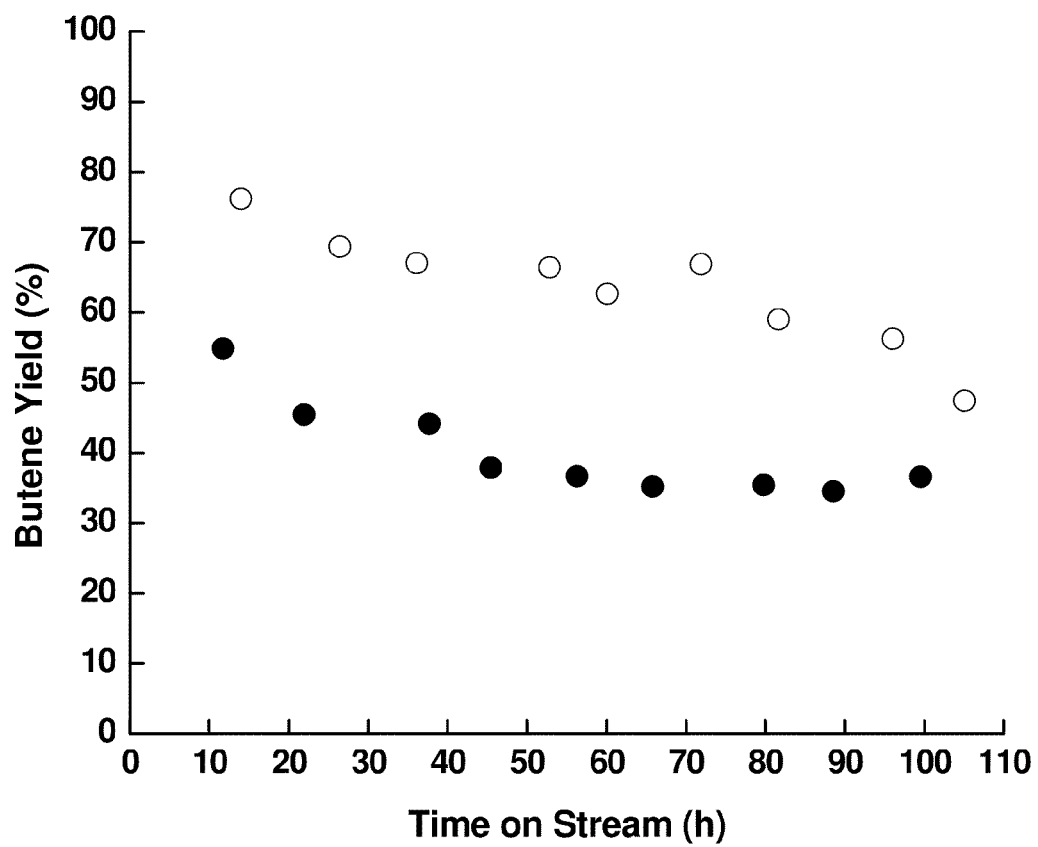
FIG. 3 is a graph depicting yield of butene versus time on stream for converting GVL to butene at 36 bar (3.6 MPa) and WHSV=0.9 $h^{-1}$ over $SiO_2/Al_2O_3$ at 648 K (●) and 673 K (○).

Production of Butene from GVL:

FIG. 3 illustrates the yield of butene (mol %, Y-axis) from GVL over $SiO_2/Al_2O_3$ at 648 K (●) and 673 K (○) plotted versus time on stream (hours, X-axis). Both reactions were conducted at 36 bar (3.6 MPa) and a WHSV of 0.9 $h^{-1}$. The catalyst initially shows higher activity at 648 K (●), which decreases to a stable yield after 40 hours of time on stream. At 673 K (○) the catalyst shows continued deactivation. The activity can be restored by calcination in air at 723 K.

Figure 4:
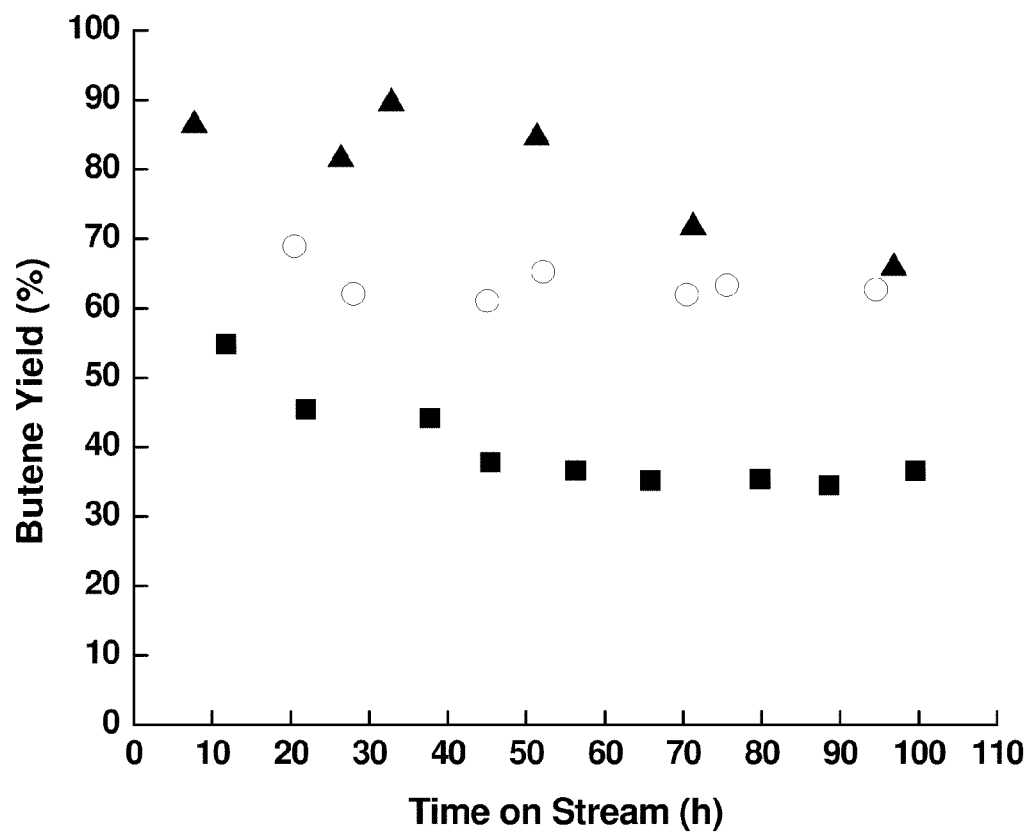
FIG. 4 is a graph depicting yield of butene versus time on stream for converting GVL to butene at 648 K, 36 bar (3.6 MPa) and WHSV=0.9 $h^{-1}$ over $SiO_2/Al_2O_3$ at various GVL concentrations: 30 wt % (■), 60 wt % (○), and 80 wt % (▲).

FIG. 4 illustrates the yield (mol %, Y-axis) of butene from GVL over $SiO_2/Al_2O_3$ at feed concentrations of 30 wt % (■), 60 wt % (○), and 80 wt % (▲) GVL versus time on stream (hours, X-axis). Reaction temperature, pressure, and WHSV were constant at 648 K, 36 bar, and 0.9 $h^{-1}$ respectively. For feeds containing 30 and 60 wt % GVL, the catalyst initially shows a loss of activity, but achieves stable catalytic activity after 40 hours of time on stream. At 80 wt % GVL, a steady decline in the butene yield is observed. The activity is recovered after calcination in air at 723 K. Experiments conducted using a pure GVL feed (results not shown) led to extensive formation of coking/polymerization products in the reactor, indicating that small amounts of water in the GVL feed are beneficial (but not required) for achieving stable catalyst performance.

Figure 5:
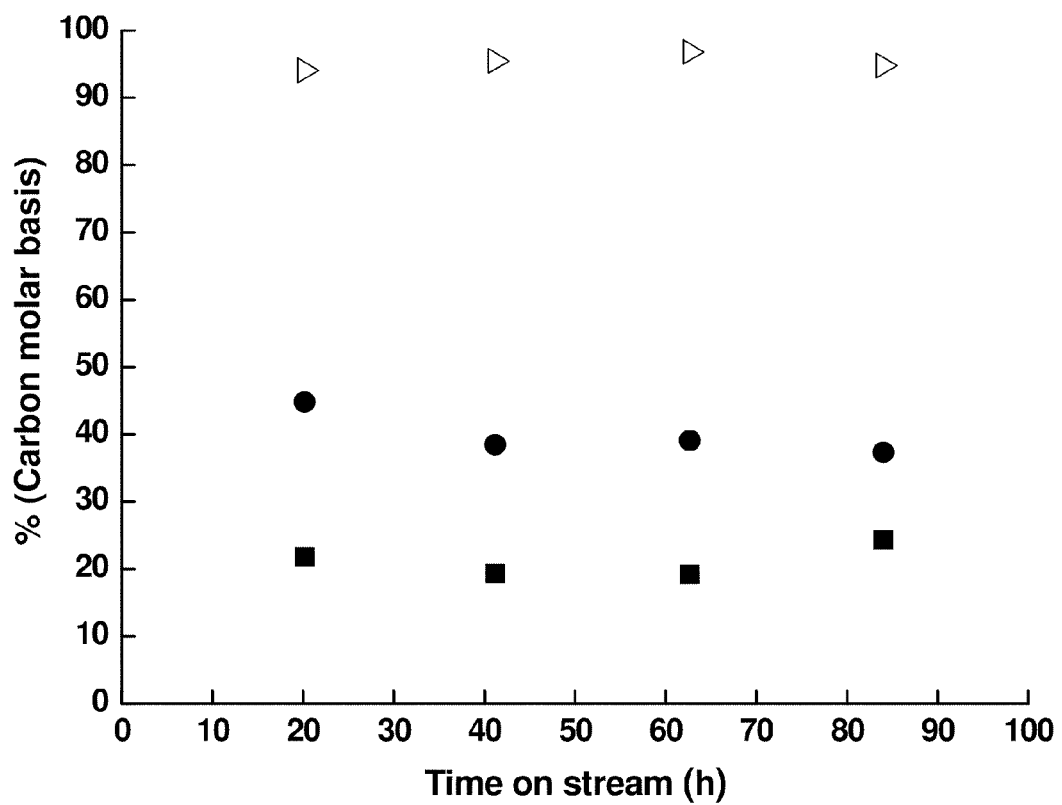
FIG. 5 is a graph depicting yield of butene from GVL in reactor 1, butene conversion in reactor 2, and overall yield of liquid $C_{8+}$ alkenes from GVL in the integrated process disclosed herein versus the time on stream. The first reactor operated at 36 bar, 648 K and 0.18 $h^{-1}$. The first separator operated at 36 bar and 383 K. The second reactor operated at 36 bar, 498 K, and 14 g HZSM-5. The second separator operated at 36 bar and 298 K. Butene yield (•), butene conversion (▷), yield to $C_{8+}$ alkenes (■).

Integrated Butene Production and Oligomerization:

FIG. 5 shows results for the integrated catalytic system for GVL conversion (% conversion, carbon molar basis, Y-axis) versus time on stream (hours, X-axis) using $SiO_2/Al_2O_3$ as the catalyst in the GVL decarboxylation reactor and HZSM-5 in the butene oligomerization reactor. Butene yield (●), butene conversion (▷), yield to $C_{8+}$ alkenes (■). It can be seen from FIG. 5 that the GVL and butene conversions are stable for more than 80 hours of time on stream, during which 90% of the butene formed in the first reactor is converted to hydrocarbons larger than $C_8$. The first reactor operated at 36 bar, 648 K and 0.18 $h^{-1}$. The first separator operated at 36 bar and 383 K. The second reactor operated at 36 bar, 498 K, and 14 g HZSM-5. The second separator operated at 36 bar and 298 K. This graph is significant in that it demonstrates that the integrated system described herein functions to make alkenes that are suitable for use as transportation fuels.

Mechanistic Considerations:

Table 4 summarizes conversions and product yields for a variety of organic acids and lactones at 648 K and 1 bar pressure over $SiO_2/Al_2O_3$. Comparable conversions are achieved for each of the lactones and the three isomers of pentenoic acid. In contrast, studies of pentanoic acid at these reaction conditions did not lead to the production of butane and $CO_2$, suggesting that substrates appropriate for decarboxylation either possess a C=C double bond (pentenoic acids) or exist as cyclic esters (lactones). While not being limited to any particular mechanism or underlying reaction pathway, it is proposed that these substrates are initially protonated by an acidic catalyst, and the decarboxylation of either valerolactones or pentenoic acids proceeds through a series of proton transfer steps to ultimately yield butene and an equivalent quantity of $CO_2$ as shown in Schemes 1 and 2:

Scheme 1: Conversion of GVL to 1-butene and $CO_2$

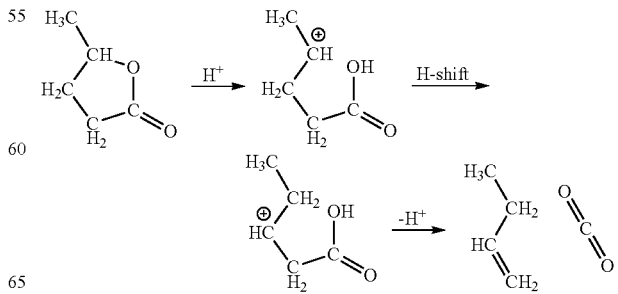

Scheme 2: Conversion of 3-penenoic acid to 1-butene and $CO_2$

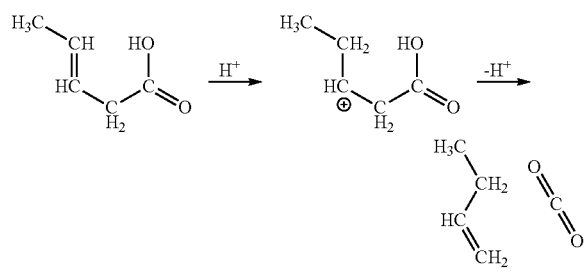

The yields of butene and the $CO_2$ co-product were slightly higher (42-48%) for the pentenoic acid feeds than for the lactone feeds (22-29%), suggesting that GVL decarboxylation proceeds through a pentenoic acid intermediate or that pentenoic acid is produced in parallel with butene from protonated intermediates. The observation of a significant quantity of GVL in the product distribution of those experiments beginning with pentenoic acids supports the reversibility of GVL ring-opening and reinforces the involvement of pentenoic acid in the mechanism of GVL decarboxylation. Based on the mechanistic considerations outlined in this section, the process can be extended to any other lactones, unsaturated carboxylic acids, or hydroxy-carboxylic acids, which would all decarboxylate through a similar pathway. A final entry documenting a comparable olefin yield (pentene) from ECL supports the extension of the process to feeds with various numbers of carbon atoms to yield various olefins.

TABLE 4

Decarboxylation of various feeds (20 wt %) at 648 K, 1 bar over $SiO_2/Al_2O_3$.

| Feed | WHSV ($h^{-1}$) | Conversion (%) | Butene Yield (%) | PA Yield (%) | GVL Yield (%) |
|---|---|---|---|---|---|
| GVL | 0.19 | 67 | 29 | 33 | 38 |
| DVL | 0.19 | 65 | 22 | 35 | 30 |
| 2-Pentenoic Acid | 0.18 | 71 | 43 | 29 | 28 |
| 3-Pentenoic Acid | 0.18 | 71 | 42 | 29 | 25 |
| 4-Pentenoic Acid | 0.18 | 71 | 48 | 30 | 22 |
| Pentanoic Acid | 0.19 | <5 | <1* | 95† | 0 |
| ECL | 0.19 | >99 | 19¹ | 44² | 35³ |

TABLE 4-continued

Decarboxylation of various feeds (20 wt %) at 648 K, 1 bar over $SiO_2/Al_2O_3$.

| Feed | WHSV ($h^{-1}$) | Conversion (%) | Butene Yield (%) | PA Yield (%) | GVL Yield (%) |
|---|---|---|---|---|---|

*Yield to Butane,
†Yield to Pentanoic Acid
¹Yield to Pentene,
²Yield to Hexenoic Acid,
³Yield to gamma-caprolactone Oligomerization Product Distributions:

Conditions used for the oligomerization reaction favor C=C double bond and skeletal isomerization. The liquid collected is a mixture of branched and linear isomers. In view of the large number of possible isomers for $C_{8+}$ alkenes, the product distribution has been described by grouping according to the number of carbon atoms. Table 5 shows the carbon distribution for the reactions included in Table 3. (In these distributions of oligomers, approximately 20% of the carbon included as $C_8$ compounds is comprised of $C_9$-$C_{11}$ compounds, and approximately 5% of the carbon included as $C_{12}$ compounds is comprised of $C_{13}$-$C_{15}$ compounds). It can be seen that the carbon distribution depends mainly on the butene conversion. At low butene conversions (entry 2 for HZSM-5 and entry 5 for "AMBERLYST"-brand resin) the products are mainly in the range $C_8$-$C_{15}$. When the butene conversion is over 90%, the carbon distribution changes to larger alkenes, thus increasing the amount of $C_{20}$ and $C_{24}$.

TABLE 5

Carbon distribution for the liquid collected after oligomerization of butene in the integrated catalytic system.

| | Catalyst | T (K) | Butene conversion (%) | $C_{<8}$ | $C_8$ | $C_{12}$ | $C_{16}$ | $C_{20}$ | $C_{24}$ |
|---|---|---|---|---|---|---|---|---|---|
| 1* | HZSM-5 (14 g) | 498 | 95 | 7 | 23 | 22 | 20 | 13 | 15 |
| 2† | HZSM-5 (14 g) | 498 | 44 | 12 | 43 | 25 | 11 | 6 | 3 |
| 3‡ | Amberlyst (3 g) | 443 | 92 | 4 | 21 | 27 | 27 | 13 | 8 |
| 4‡ | Amberlyst (4 g) | 443 | 94 | 7 | 20 | 22 | 26 | 17 | 8 |
| 5§ | Amberlyst (4 g) | 443 | 81 | 11 | 29 | 26 | 20 | 10 | 4 |
| 6‖ | Amberlyst (12 g) | 443 | 90 | 7 | 23 | 26 | 25 | 13 | 6 |

*Reactor 1: 2.7 g $SiO_2$—$Al_2O_3$. WHSV = 0.68 $h^{-1}$. First separator at 373 K.
†Reactor 1: 10 g $SiO_2$—$Al_2O_3$. WHSV = 0.18 $h^{-1}$. First separator at 383 K.
‡Reactor 1: 10 g $SiO_2$—$Al_2O_3$. WHSV = 0.18 $h^{-1}$. First separator at 388 K.
§Reactor 1: 10 g $SiO_2$—$Al_2O_3$. WHSV = 0.22 $h^{-1}$. First separator at 398 K.
‖Reactor 1: 8 g $SiO_2$—$Al_2O_3$. WHSV = 0.22 $h^{-1}$. First separator at 398 K.

BIBLIOGRAPHY

1. E. L. Kunkes et al., *Science* 322, 417-421 (2008).
2. A. J. Ragauskas et al., *Science* 311, 484-489 (2006).
3. G. W. Huber, S. Iborra, A. Corma, *Chem. Rev.* 106, 4044-4098 (2006).
4. D. A. Simonetti, J. Rass-Hansen, E. L. Kunkes, R. R. Soares, J. A. Dumesic, *Green Chem.* 9, 1073-1083 (2007).
5. G. W. Huber, B. E. Dale, *Sci. Am.* 301, 52 (July 2009).
6. I. T. Horvath, H. Mehdi, V. Fabos, L. Boda, L. T. Mika, *Green Chem.* 10, 238-242 (2008).
7. H. Mehdi et al., *Top. Catal.* 48, 49-54 (2008).
8. L. E. Manzer, *Appl. Catal. A-General* 272, 249-256 (2004).
9. S. W. Fitzpatrick, "Final Technical Report Commercialization of the Biofine Technology for Levulinic Acid Production from Paper Sludge" *Tech. Report No. DOE/CE/41178* (BioMetics, Inc, 2002). http://www.osti.gov/bridge
10. H. Heeres et al., *Green Chem.* 11, 1247-1255 (2009).
11. I. Ahmed. U.S. Pat. No. 6,190,427 (2001).

12. D. C. Elliott, J. G. Frye. U.S. Pat. No. 5,883,266 (1999)
13. G. W. Huber "Breaking the Chemical and Engineering Barriers to Lignocellulosic Biofuels: Next Generation Hydrocarbon Biorefineries" (U. Massachusetts Amherst, 2007). http://www.ecs.umass.edu/biofuels/Images/Roadmap2-08.pdf
14. R. S. Haszeldine, Science 325, 1647-1652 (2009).
15. K. S. Lackner, *Science* 300, 1677-1678 (2003).
16. H. Sakurai, M. Haruta, *Catal. Today* 29, 361-365 (1996).
17. J. Toyir, P. R. de la Piscina, J. L. G. Fierro, N. Homs, *Appl. Catal. B-Environ.* 34, 255-266 (2001).
18. S. Koppatz et al., *Fuel Processing Technology* 90, 914-921 (2009).
19. R. D. Cortright, R. R. Davda, J. A. Dumesic, *Nature* 418, 964-967 (2002).
20. G. W. Coates, D. R. Moore, *Angew. Chem. Int. Ed* 43, 6618-6639 (2004).
21. D. J. Darensbourg, *Chem. Rev.* 107, 2388-2410 (2007).
22. M. Wick, J. M. Lebeault, *Appl. Microbiol. Biotech.* 56, 687-692 (2001).
24. S. Matar, L. F. Hatch, *Chemistry of Petrochemical Processes.* (G. P. Company, Houston, ed. 2, 2000), pp. 248-250.
25. J. Cejka, H. van Bekkum, A. Corma, F. Schuth, *Introduction to Zeolite Science and Practice*, (Elsevier, 3$^{rd}$ Revised Edition, 2007), pp. 895-899
26. A. Mantilla et al., *Catal. Today* 107-08, 707-712 (2005).
27. R. J. Quann, L. A. Green, S. A. Tabak, F. J. Krambeck, Ind. Eng. Chem. Res. 27, 565-570 (1988).
28. G. Centi, R. Van Santen, Catalysis for Renewables: From Feedstock to Energy Production (Wiley-VCH, Wienheim, 2007), pp. 137.
29. J. Skupinska, Chem. Rev 91, 613-648 (1991).

What is claimed is:

1. A process for producing hydrocarbons, the process comprising:
   (a) reacting lactones, hydroxy-carboxylic acids, alkene-carboxylic acids, or mixtures thereof, or an aqueous solution comprising lactones, hydroxy-carboxylic acids, alkene-carboxylic acids, or mixtures thereof with a first acid catalyst, at a first temperature, and a first pressure, to yield a first product mixture comprising olefins; and then
   (b) reacting the first product mixture with a second acid catalyst, at a second temperature, and a second pressure, to yield a second product mixture comprising hydrocarbons heavier than the olefins in the first product mixture.

2. The process of claim 1, wherein step (b) comprises reacting the first product mixture to yield a second product mixture comprising alkenes having a chain length of $C_8$ or greater.

3. The process of claim 1, further comprising, after step (a) and before step (b) separating from the first product mixture at least a fraction of any water present therein.

4. The process of claim 1, wherein the first temperature and the second temperature are the same or are different.

5. The process of claim 1, wherein the first pressure and the second pressure are the same or are different.

6. The process of claim 1, where the first and second acid catalysts are solid acid catalysts.

7. The process of claim 1, wherein the first acid catalyst and the second acid catalyst are the same or are different.

8. The process according to claim 1, wherein the first pressure and the second pressure, which may be the same or different, range from atmospheric to about 100 bar, the first temperature ranges from about 500 K to about 1000 K, and the second temperature ranges from about 300 K to about 800 K.

9. The process according to claim 1, wherein the first pressure and the second pressure, which may be the same or different, range from about 15 bar to about 50 bar, the first temperature ranges from about 550 K to about 750 K, and the second temperature ranges from about 300 K to about 750 K.

10. The process according to claim 1, wherein the first pressure and the second pressure, which may be the same or different, range from about 25 bar to about 45 bar, the first temperature ranges from about 600 K to about 700 K, and the second temperature ranges from about 350 K to about 600 K.

11. The process according to claim 1, comprising conducting steps (a) and (b) at a weight hourly space velocity of from about 0.05 h$^{-1}$ to about 5.0 h$^{-1}$.

12. The process according to claim 1, comprising, in step (a), reacting an aqueous solution of lactone.

13. The process according to claim 1, comprising, in step (a), reacting an aqueous solution of gamma-valerolactone.

14. The process according to claim 1, further comprising, after step (b):
   (c) separating at least a fraction of any carbon dioxide present in the second product mixture.

15. The process according to any one of claims 1 through 14, wherein the process is conducted in an integrated reactor comprising a first reaction chamber in which step (a) is conducted, and a second reaction chamber, operationally connected to the first, in which step (b) is conducted.

16. The process according to claim 15, wherein the process is conducted in an integrated reactor further comprising a phase separator operationally disposed between the first reaction chamber and the second reaction chamber, wherein the phase separator is configured to separate at least a fraction of any water present in the first product mixture.

17. A process for producing alkenes having a chain length of C8 or greater, the process comprising:
   (a) reacting lactones, hydroxy-carboxylic acids, alkene-carboxylic acids, or mixtures thereof, or an aqueous solution comprising lactones, hydroxy-carboxylic acids, alkene-carboxylic acids, or mixtures thereof with a first acid catalyst, at a first temperature, and a first pressure, to yield a first product mixture comprising olefins; and
   then
   (b) separating from the first product mixture at least a fraction of any water present therein; and then
   (c) reacting the first product mixture with a second acid catalyst, at a second temperature, and a second pressure, to yield a second product mixture comprising alkenes having a chain length of C8 or greater;
   wherein the process is conducted in an integrated reactor comprising
   (i) a first reaction chamber in which step (a) is conducted;
   (ii) a phase separator in which step (b) is conducted, wherein the phase separator is operationally connected to the first reaction chamber; and
   (iii) a second reaction chamber in which step (c) is conducted, wherein the second reaction chamber is operationally connected to the phase separator.

18. The process of claim 17, where the first and second acid catalysts are solid acid catalysts.

19. The process of claim 18, wherein the first acid catalyst and the second acid catalyst are the same or are different.

20. The process according to claim 18, wherein the first pressure and the second pressure, which may be the same or different, range from atmospheric to about 100 bar, the first temperature ranges from about 500 K to about 1000 K, and the second temperature ranges from about 300 K to about 800 K.

21. The process according to claim 18, wherein the first pressure and the second pressure, which may be the same or different, range from about 15 bar to about 50 bar, the first temperature ranges from about 550 K to about 750 K, and the second temperature ranges from about 300 K to about 750 K.

22. The process according to claim 18, wherein the first pressure and the second pressure, which may be the same or different, range from about 25 bar to about 45 bar, the first temperature ranges from about 600 K to about 700 K, and the second temperature ranges from about 350 K to about 600 K.

23. The process according to claim 18, comprising conducting steps (a) and (b) at a weight hourly space velocity of from about 0.05 $h^{-1}$ to about 5.0 $h^{-1}$.

\* \* \* \* \*